(12) United States Patent
Call (10) Patent No.: US 7,351,223 B2
(45) Date of Patent: Apr. 1, 2008

(54) INFUSION SYRINGE WITH INTEGRATED PRESSURE TRANSDUCER

(75) Inventor: Evan W. Call, Bountiful, UT (US)

(73) Assignee: Physicians Industries, Inc., West Valley City, UT (US)

( * ) Notice: Subject to any disclaimer, the term of this patent is extended or adjusted under 35 U.S.C. 154(b) by 85 days.

(21) Appl. No.: 10/769,634

(22) Filed: Jan. 30, 2004

(65) Prior Publication Data

US 2004/0260238 A1 Dec. 23, 2004

Related U.S. Application Data

(60) Provisional application No. 60/468,398, filed on May 5, 2003.

(51) Int. Cl.
*A61M 29/00* (2006.01)

(52) U.S. Cl. .................................................. 604/97.03

(58) Field of Classification Search ........... 604/100.01, 604/187, 65, 67, 96–100, 100.03, 118, 19; 128/748
See application file for complete search history.

(56) References Cited

U.S. PATENT DOCUMENTS

| | | | |
|---|---|---|---|
| 3,625,793 A | 12/1971 | Sheridan | |
| 3,878,830 A | 4/1975 | Bicher | |
| RE30,365 E | 8/1980 | Mattler | |
| 4,370,982 A | 2/1983 | Reilly | |
| 4,439,185 A | 3/1984 | Lundquist | |
| 4,583,974 A * | 4/1986 | Kokernak | .................... 604/211 |
| 4,651,738 A | 3/1987 | Demer et al. | |
| 4,655,749 A * | 4/1987 | Fischione | ................ 604/97.03 |
| 4,710,179 A | 12/1987 | Haber et al. | |
| 4,723,938 A | 2/1988 | Goodin et al. | |
| 4,740,203 A | 4/1988 | Hoskins et al. | |
| 4,758,223 A | 7/1988 | Rydell | |
| 4,810,249 A | 3/1989 | Haber et al. | |
| 4,815,313 A * | 3/1989 | Beard | ......................... 73/1.62 |
| 4,832,692 A | 5/1989 | Box et al. | |
| 4,873,986 A * | 10/1989 | Wallace | ...................... 600/483 |
| 4,919,121 A | 4/1990 | Rydell et al. | |
| 4,940,459 A | 7/1990 | Noce | |
| 4,951,677 A | 8/1990 | Crowley et al. | |
| 5,004,472 A | 4/1991 | Wallace | |
| 5,009,662 A | 4/1991 | Wallace et al. | |
| 5,019,041 A | 5/1991 | Robinson et al. | |
| 5,021,046 A | 6/1991 | Wallace | |

(Continued)

*Primary Examiner*—Nicholas D. Lucchesi
*Assistant Examiner*—Christopher D. Koharski
(74) *Attorney, Agent, or Firm*—Kirton & McConkie; David B. Tingey (57) ABSTRACT

A device for measuring fluid pressure in the lumen of a syringe including a pressure transducer integrally mounted in the plunger of the syringe under the plunger tip, such that the force applied by the plunger to the fluid in the syringe is transmitted to the transducer and the resulting electronic signal is converted to a display value for aiding a physician. A syringe that includes such a device may be placed in communication with a tubular member attached to a needle inserted into the body of a disk found in the spinal column of the back for diagnosing diseased disks in the back. The displayed pressure value may facilitate this diagnosis. Other uses of pressure applying monitoring syringes for other applications in communication with the body also benefit from the disclosed syringe construction, such as percutaneous translumenal angioplasty (PTA) procedures.

14 Claims, 9 Drawing Sheets

U.S. PATENT DOCUMENTS

| | | |
|---|---|---|
| 5,047,015 A | 9/1991 | Foote et al. |
| 5,057,078 A * | 10/1991 | Foote et al. .............. 604/99.01 |
| 5,084,060 A | 1/1992 | Freund et al. |
| 5,137,514 A | 8/1992 | Ryan |
| 5,147,300 A | 9/1992 | Robinson et al. |
| 5,168,757 A | 12/1992 | Rabenau et al. |
| 5,201,753 A | 4/1993 | Lampropoulos et al. |
| 5,209,732 A | 5/1993 | Lampropoulos et al. |
| 5,213,115 A * | 5/1993 | Zytkovicz et al. .......... 128/898 |
| 5,215,523 A | 6/1993 | Williams et al. |
| 5,232,024 A | 8/1993 | Williams |
| 5,246,011 A * | 9/1993 | Caillouette .................. 600/566 |
| 5,273,537 A | 12/1993 | Haskvitz et al. |
| 5,318,534 A | 6/1994 | Williams et al. |
| 5,383,855 A | 1/1995 | Nicholson et al. |
| 5,385,549 A | 1/1995 | Lampropoulos et al. |
| 5,387,194 A * | 2/1995 | Williams et al. ......... 604/97.03 |
| 5,403,274 A | 4/1995 | Cannon |
| 5,425,713 A | 6/1995 | Taylor et al. |
| 5,429,606 A | 7/1995 | Robinson et al. |
| 5,431,629 A | 7/1995 | Lampropoulos et al. |
| 5,433,707 A | 7/1995 | Call |
| 5,449,344 A | 9/1995 | Taylor et al. |
| 5,449,345 A * | 9/1995 | Taylor et al. .......... 604/100.03 |
| 5,453,091 A | 9/1995 | Taylor et al. |
| 5,458,571 A | 10/1995 | Lampropoulos et al. |
| 5,459,700 A | 10/1995 | Jacobs |
| 5,460,609 A | 10/1995 | O'Donnell |
| 5,472,424 A | 12/1995 | Lampropoulos et al. |
| 5,489,256 A | 2/1996 | Adair |
| 5,545,133 A | 8/1996 | Burns et al. |
| 5,562,614 A | 10/1996 | O'Donnell |
| 5,599,301 A | 2/1997 | Jacobs et al. |
| 5,625,144 A | 4/1997 | Chang |
| 5,647,847 A | 7/1997 | Lafontaine et al. |
| 5,685,848 A | 11/1997 | Robinson et al. |
| 5,695,468 A | 12/1997 | Lafontaine et al. |
| 5,704,913 A | 1/1998 | Abele et al. |
| 5,728,064 A | 3/1998 | Burns et al. |
| 5,741,229 A | 4/1998 | Robinson et al. |
| 5,749,853 A | 5/1998 | O'Donnell et al. |
| 5,752,935 A | 5/1998 | Robinson et al. |
| 5,785,685 A | 7/1998 | Kugler et al. |
| 5,808,203 A * | 9/1998 | Nolan et al. .................. 73/700 |
| 5,860,955 A | 1/1999 | Wright et al. |
| 5,891,089 A | 4/1999 | Katz et al. |
| 5,951,517 A | 9/1999 | Lampropoulos et al. |
| 5,968,017 A | 10/1999 | Lampropoulos et al. |
| 6,139,523 A | 10/2000 | Taylor et al. |
| 6,179,815 B1 | 1/2001 | Foote |
| 6,190,354 B1 | 2/2001 | Sell et al. |
| 6,224,561 B1 * | 5/2001 | Swendson et al. .......... 600/562 |
| 6,245,043 B1 | 6/2001 | Villette |
| 6,394,977 B1 | 5/2002 | Taylor et al. |
| 6,792,306 B2 | 9/2004 | Henley et al. |
| 2003/0216692 A1 | 11/2003 | Fago et al. |
| 2004/0024361 A1 | 2/2004 | Fago et al. |

* cited by examiner

INFUSION SYRINGE WITH INTEGRATED PRESSURE TRANSDUCER

CROSS-REFERENCE TO RELATED APPLICATION

This application claims the benefit of U.S. Provisional Application 60/468,398, filed May 5, 2003, the contents of the entirety of which are hereby incorporated herein in their entirety by this reference.

BACKGROUND OF THE INVENTION

1. Field of the Invention

This invention relates to an infusion syringe apparatus for applying and monitoring fluid pressure applied to the inter-vertebral disk of the spinal column, or more specifically, monitoring of the pressure applied through a needle or cannula through the annulus fibrosus of the disk and into the nucleus pulposus thus allowing the diagnosis of diseased or ruptured disks. The field may further include fluid pressure-inducing syringes and methods involved in percutaneous translumental angioplasty (PTA) procedures.

2. State of the Art

Infusers utilized in diskography and balloon angioplasty are well known and established in medical practice. The tools typically applied to angioplasty have found application in other fields as well, such as opening diseased carotid arteries and improving or reestablishing blood flow to the extremities of diabetics and similar purposes. Similar tools have been used in the field of pain diagnosis and management related to orthopedic procedures related to the spine.

The number of failed or ineffectual spine surgeries has driven the development of new techniques for verifying the location of damage or injury in the vertebral column. Typically, these procedures involve the insertion of a curved or specifically shaped cannula or needle under the transverse process of the vertebra and around the inferior articular process and penetrate the annulus fibrosus. Application of fluid pressure to the nucleus pulposus will either go undetected, create relief from chronic pain, or induce a pain episode due to the pinching of a nerve. By the application of this technique to suspect vertebral disks, a physician can identify the pain locus and thus use the appropriate intervention to provide relief for the patient. This process is typically performed utilizing ionic contrast media, typically made from ionically bound iodine. This media allows the physician to view the procedure on a fluoroscope which aids in needle positioning and visual diagnosis. Diagnosis is based on the inter-vertebral disks' ability, or inability, to contain the contrast media when it is injected under pressure into the nucleus pulposus of the disk.

Typically, any syringe with a mechanism for measuring pressure has been used to measure the patency of the inter-vertebral disk. However, such syringes typically utilize a transducer mounted at the distal end of the syringe barrel which is in communication with the fluid path of the syringe. The presence of a non-transparent transducer and associated fixtures adjacent the fluid path prevents clear vision of bubbles in the contrast media or other imperfections that may be of concern in interventional procedures. Such devices are described in U.S. Pat. Nos. 5,021,046 and 5,084,060. Also, many such devices are awkward to use, are unduly complex or fail to provide a flexible fluid pressure adjustment.

BRIEF SUMMARY OF THE INVENTION

The instant invention involves a hand-operated syringe for applying pressure to a fluid within the syringe which pressurized fluid interacts, directly or indirectly, with some physiology of the human body. The syringe has a barrel, preferably constructed of a transparent rigid material. A plunger adapted to slide within the barrel and to apply pressure to fluid within the barrel is constructed to have two operative motions: 1) a first sliding motion induced by direct hand motion, e.g., thumb force, at the proximal end of the plunger, or some plunger extension attached generally axially to the proximal end of the plunger, whereby a rapid increase or decrease in the fluid pressure can be controllably caused to occur within the syringe barrel and 2) a second motion, wherein the plunger is not freely slidable but has threads which interact with an adjustment mechanism, wherein the adjustment mechanism is engageable and disengageable to permit minute axial motion of the plunger and thus adjusts the applied fluid pressure in controlled micro pressure adjustments.

The adjustment mechanism includes means whereby the threads on the plunger may be rapidly (e.g., instantaneously) disengaged to permit the plunger to slide freely thereby instantaneously releasing the fluid pressure within the syringe barrel. The adjustment mechanism engages threads on the plunger or on a casing (sleeve) associated with and enveloping at least a portion of the plunger's external surface.

A further feature of the syringe is a pressure monitoring system whereby the pressure of the fluid within the barrel may be observed and, by appropriate adjustment of the plunger, such pressure controllably increased, decreased or released.

Since it is desired generally to monitor applied fluid pressure, a pressure sensitive transducer is fitted to communicate directly, or indirectly, with the fluid within the syringe barrel. Such transducers have conventionally been attached to the barrel generally at or near the distal end of the barrel as illustrated in U.S. Pat. Nos. 5,021,046; 5,009,662 and 5,004,472 to Wallace. While such positioning of the pressure sensitive transducer is acceptable for many purposes, the transducer and its associated fittings are not transparent and block the vision of a syringe operator of the fluid within that portion of the barrel adjacent the transducer. This may often be very disadvantageous if air bubbles exist within the fluid within the syringe barrel or within the tubing leading to a patient's body especially where the fluid is intended to enter a portion of the body such as occurs with fluid injection into a spinal disk.

A significant advantage is realized by attaching the transducer to the distal end (pressure tip) of the plunger and having at least a part of the electronics which are part of the pressure-monitoring apparatus contained within the body of the plunger. Such a transducer and electronics arrangement is especially useful inasmuch as the electronics may emit a wireless signal to cause a pressure reading to occur on a remote display, i.e., a display located on the exterior of the syringe barrel or a remote display not attached to the syringe barrel, including a display positioned at or near the proximal end of the syringe plunger or an extension attached thereto.

One very advantageous arrangement is to have all the necessary electronics to be contained within the syringe plunger and have a display incorporated in the plunger and positioned at or near the proximal end of the plunger. The display is thus within the vision field of a syringe operator who is focused on the syringe fluid. The display may interact with the electronics associated with the pressure transduced by an electrical conductor or by wireless means.

DETAILED DESCRIPTION OF THE INVENTION

Figure 1:
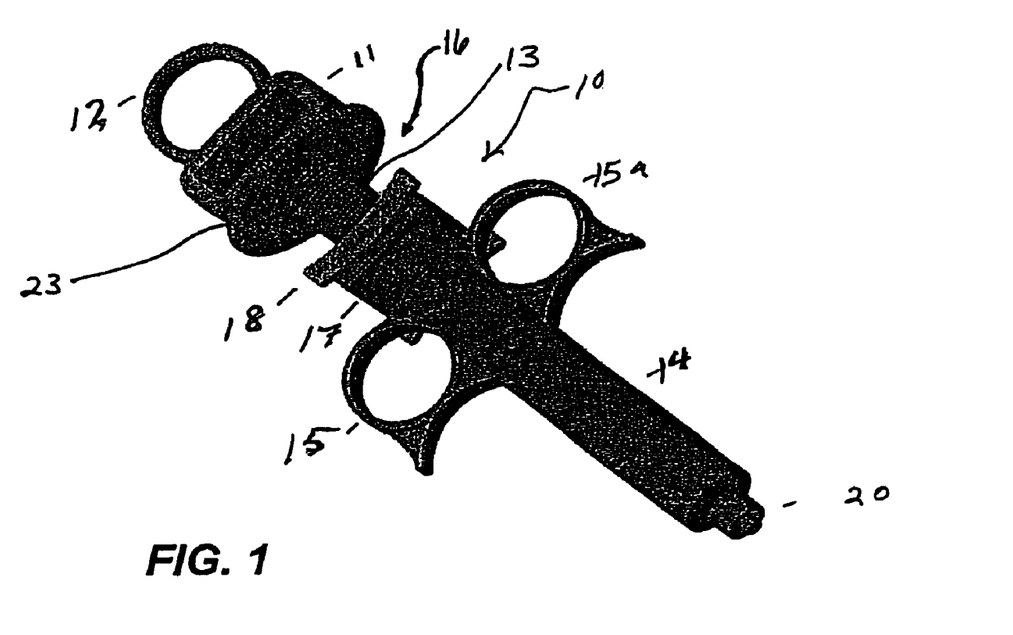
FIG. 1 is a perspective view of a syringe of the instant invention.

FIG. 1 is an external perspective view of a syringe 10 of the instant invention having the electronics housed in the plunger 11, a thumb ring 12 affixed to the proximal end of the plunger 11 for control of fluid pressure syringe 10. The plunger 11 is enveloped at least partially by a rotatable sleeve 16 with a captivated thread mechanism 13 capable of rotating independent of the plunger end cap 19 (see FIG. 4), a locking mechanism housing 17 and a sliding thread locking mechanism 18. The syringe barrel 14 is similar to one known in the art and incorporates rings 15 and 15a for the index finger and the middle finger. The triangular arrangement of the plunger thumb ring 12 and barrel rings 15 and 15a facilitates one-handed operation of the syringe. This is a great advantage for any physician or technician performing any procedure in which fluid pressure is directly or indirectly applied to any human body part including a spinal disk or an artery. It is typically advantageous to have one free hand for accomplishing other tasks during any operation of a syringe.

The syringe barrel has a luer lock or a slip socket 20 for a bonded extension line. The locking mechanism housing 17 is molded to attach to the proximal end of the syringe 10 and captivates a sliding thread locking mechanism 18 that engages or releases the threads of rotatable sleeve 16. Sliding this mechanism to one side allows the plunger 11 to travel free in the barrel 14, sliding to the other side locks the mechanism and requires that the thumbwheel 23 be rotated to generate minute movement of the plunger 11 and associated volume or pressure change in the syringe lumen.

Figure 2:
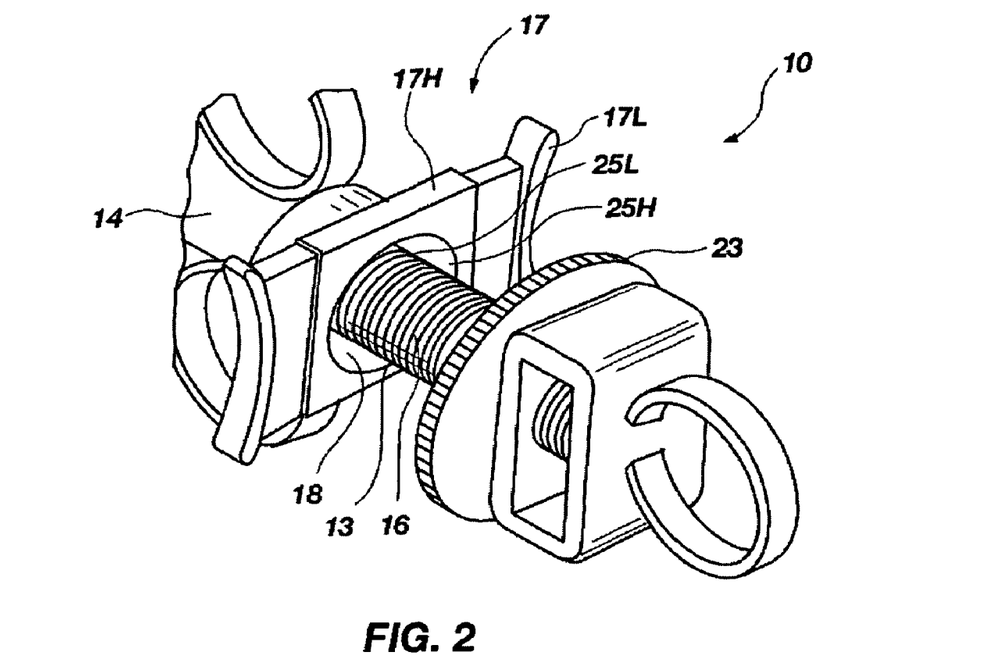
FIG. 2 is a perspective view of the proximal portion of the syringe of FIG. 1.

As illustrated in FIG. 2, the cutout 25 in the body of the sliding thread locking mechanism 18 is a keyhole-shaped opening with a minor width such that it will engage with the threads of the threaded rotatable sleeve 16 (see FIG. 3), and has sufficient relief in its major diameter to allow free travel of the plunger 11 when threads of the rotatable sleeve 16 are disengaged. Rapid disengagement is very desirable since many procedures may require an instantaneous release of fluid pressure to prevent or minimize some damage to a body part being treated or investigated.

Figure 3:
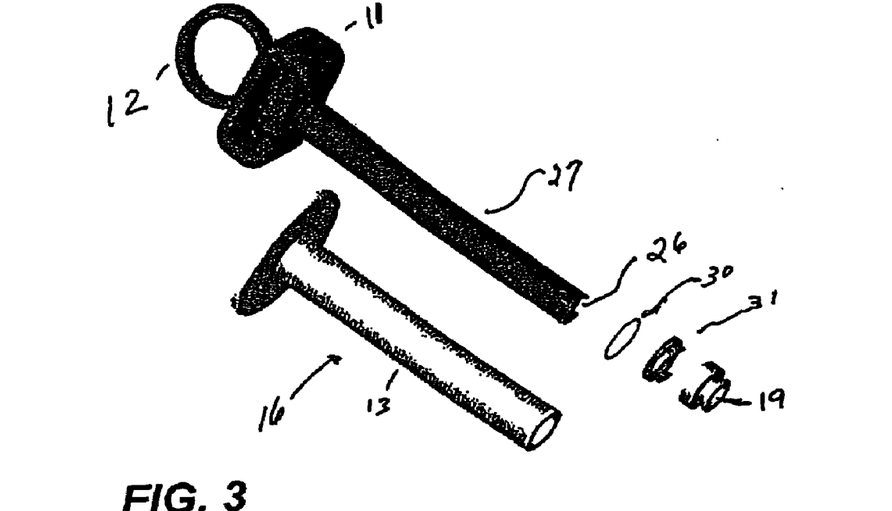
FIG. 3 is an exploded view of a syringe plunger and encasing sleeve.

The plunger of the syringe illustrated in FIG. 3 has a smooth inner bore 26 and outer bore 27. The outer bore 27 becomes the supporting surface for the rotation of the threaded rotatable sleeve 16. When the sliding thread locking mechanism 18 is engaged with the threads of the threaded sleeve, displacement of the plunger 11 is generated by rotation of the thumbwheel 23 which forces the distal end of the rotatable sleeve 16 against a flange, such as provided by plunger end cap 19 adjacent the distal end of the plunger 11. The axial advancement or retraction of the plunger 11 effected by rotation of thumbwheel 23 is very slight, thus minute adjustments of fluid pressure are readily accomplished. Also advantageous is the location of the thumbwheel 23 since its position vis-a-vis rings 15 and 15a and thumb ring 12 readily permits an operator's thumb to be removed from thumb ring 12 and placed upon thumbwheel 23 to rotate thumbwheel 23 to achieve minute fluid pressure adjustments. This continuous one-handed operation of the syringe is very advantageous for a variety of reasons.

Figure 4:
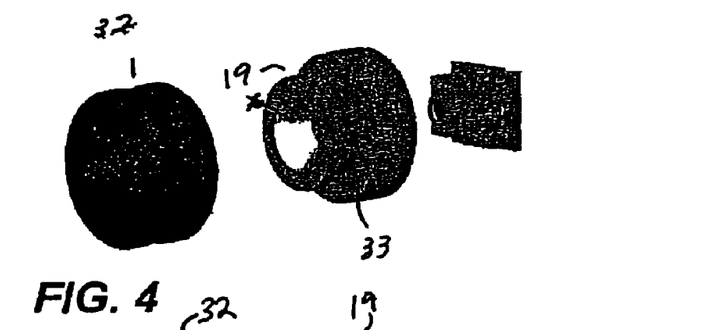
FIGS. 4 and 5 are exploded views of components associated with the plunger tip.
Figure 5:
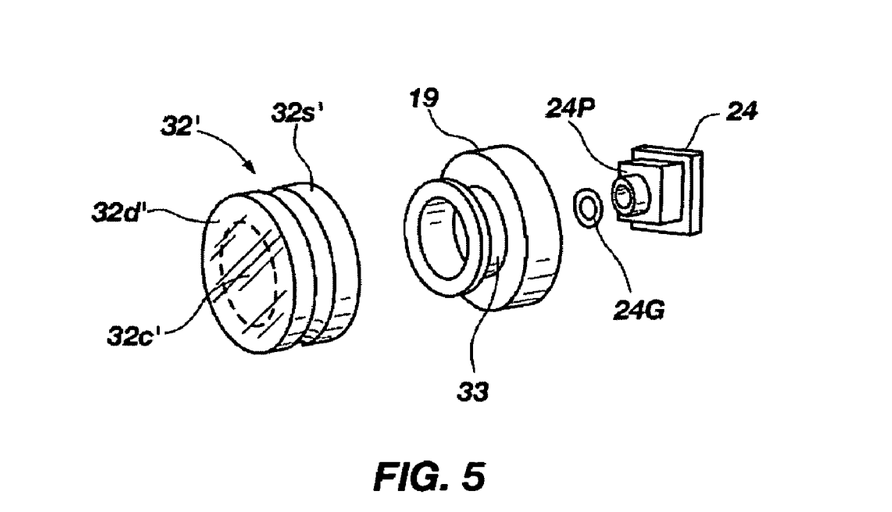

The plunger end cap 19 receives an electronic transducer, similar to those described and illustrated in the U.S. patents to Wallace, cited hereinabove, which is retained by the transducer retainer 31. The friction reduction washer 30 is placed on the plunger's smooth outer bore 27 after the threaded rotatable sleeve 16 slides over plunger 11, thus acting as a friction reducing bearing between the threaded rotatable sleeve 16 and the plunger end cap 19. The rubber plunger tip 32 is snapped over the detent 33 of the plunger end cap 19, as depicted in FIGS. 4 and 5.

The plunger tip assembly consists of a transducer that is seated within the plunger end cap 19. The cavity of the plunger end cap 19 is filled with a force transmitting silicone gel which allows the transmission of forces to the transducer. Other arrangements for appropriate attachment of the transducer to the plunger tip may, of course, be utilized.

Figure 6A:
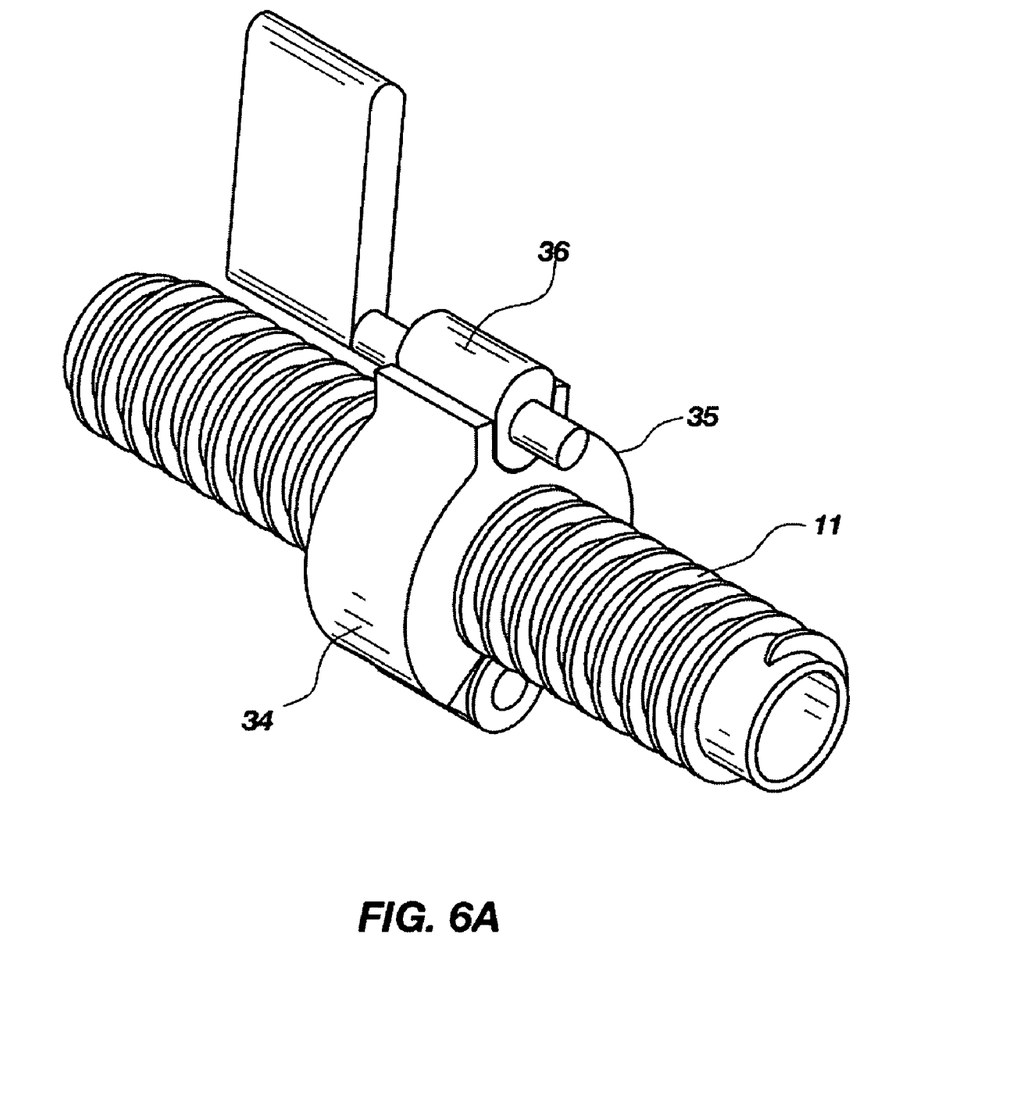
FIGS. 6A-6C include several views of a clamshell locking mechanism for a syringe of the instant invention.
Figure 6B:
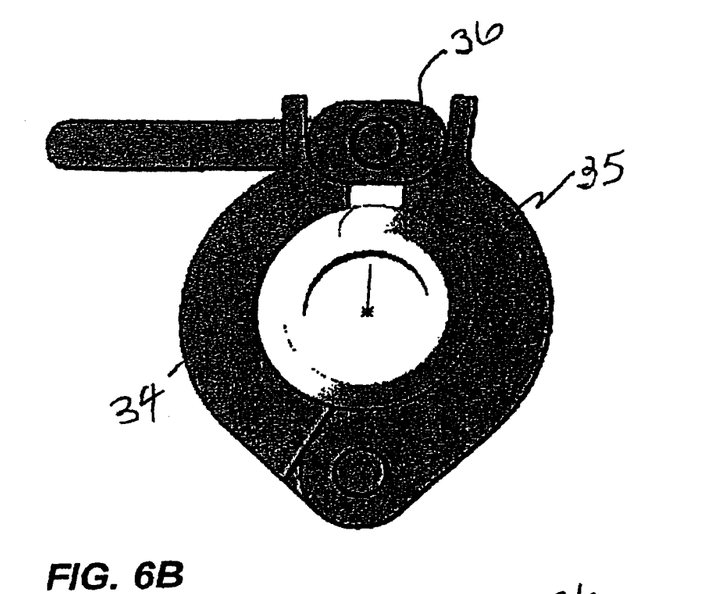
Figure 6C:
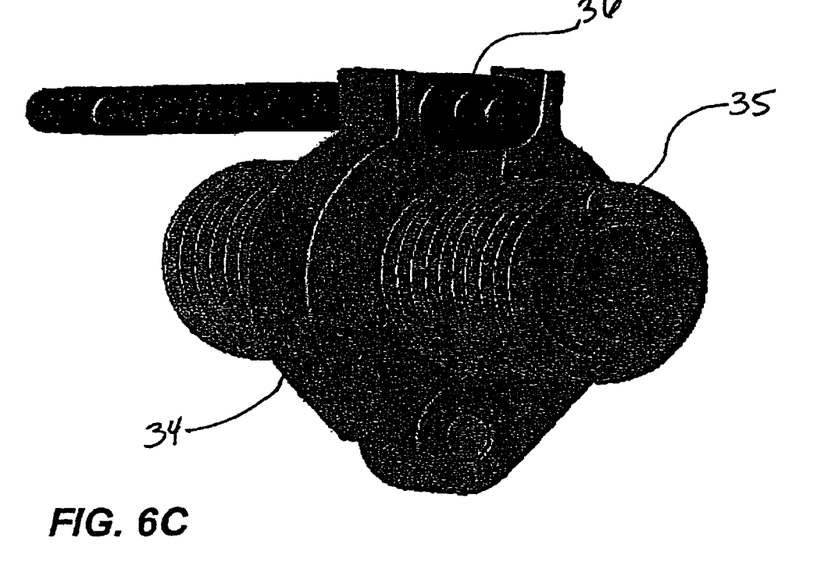

While a slide-lock mechanism has been illustrated and described herein, other locking mechanisms may be effectively utilized. For example, a two-piece clam-shell, spring-loaded mechanism such as that shown in FIGS. 6A-6C can be usefully employed. A pair of clam-shaped elements 34 and 35 are hinged at their closed end and spring-biased to be in a closed position whereby the elements 34 and 35 clamp the threaded sleeve or threaded plunger 37. A rotatable cam 36 is positioned at the open end of the clam-shaped elements 34 and 35, whereby rotation of the cam 36 forces the clam-shaped elements 34 and 35 into an "open" position whereby a threaded sleeve or plunger may slide freely. The "open" position is illustrated in FIG. 6A while FIGS. 6B and 6C illustrate the "closed" position. The transducer may also be utilized in a conventional manner, as illustrated in U.S. Pat. No. 5,004,472 to Wallace.

Other mechanisms of locking a threaded sleeve or plunger in a fixed position or to provide minute pressure adjustment may be employed, including locking mechanisms disclosed in prior patents, such as U.S. Pat. Nos. 5,860,955; 5,433,707 and 5,685,848.

Preferred locking mechanisms are those which are operable by the same hand which is otherwise holding or operating the syringe. Preferably, the locking mechanism can be set or released by the thumb of the hand engaging one or more of the finger rings of the syringe.

As stated hereinabove, having a threaded sleeve engage the locking mechanism permits minor axial adjustments of the plunger without rotation of the plunger itself which keeps a pressure readout display 39 (FIGS. 8A-8C) affixed at the proximal end of the plunger in a continuously visible position. However, if the pressure transducer and associated electronics are all incorporated as part of the plunger and the electronics send a wireless signal to a remote display, then the plunger itself may be threaded near its proximal end for engagement with a suitable locking mechanism to accomplish minute axial adjustment of the plunger which is caused by minor rotation of the plunger. A thumb ring for a thread plunger with a slightly larger open diameter may facilitate positioning of an operator's thumb even though the thumb ring may be rotated slightly. Also, a thumb ring which is fixed to a threaded plunger so the thumb ring freely rotates also accommodates plunger rotation.

Thus, a plunger which incorporates a pressure transducer and associated electronics is useful with either a threaded plunger or a threaded sleeve freely encasing the plunger.

Figure 7:
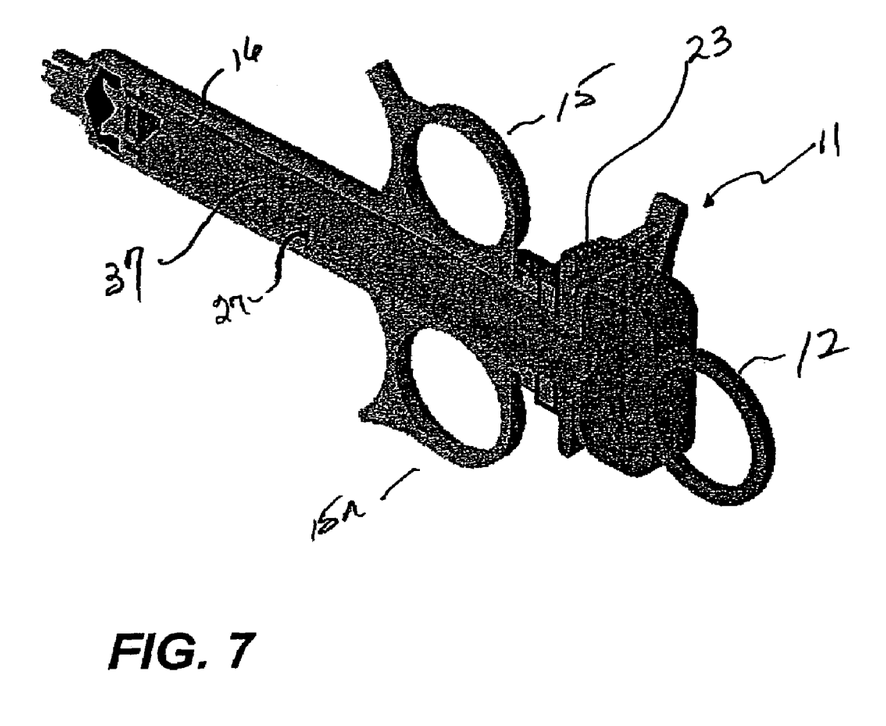
FIG. 7 is a cross-sectional perspective view of the syringe of FIG. 1.

FIG. 7 is a perspective, sectional view along a longitudinal plane encompassing the central longitudinal axis. The finger rings 15 and 15*a* and thumb ring 12 are shown at the proximal end of the syringe. The open central cavity 37 (also depicted in FIG. 6A) of the plunger is exposed. It is in this space that an electronics assembly may be incorporated to connect a pressure transducer in the plunger top to a pressure readout display located in the display holder located at the proximal end of the plunger.

The plunger 11 and its threaded rotatable sleeve 16 are illustrated in an inserted position in the syringe barrel.

The thumbwheel 23 and sliding thread locking mechanism are also illustrated. The sleeve and plunger slide longitudinally within the syringe barrel except when the sliding thread locking mechanism engages the threads of the sleeve. The thumbwheel 23 is fixed to the sleeve so that rotation of the thumbwheel 23 rotates the sleeve threads with respect to the sliding thread locking mechanism causing the plunger 11 to advance or withdraw depending upon the direction of rotation of the thumbwheel 23.

Rotation of the thumbwheel 23 while the sliding thread locking mechanism engages the threads of the sleeve causes minute longitudinal movement of the plunger, permitting minor adjustments in the fluid pressure in the barrel and attached lumen. Such precise adjustment of fluid pressure is very desirable for a number of medical procedures, such as discography and angioplasty procedures.

Fluid pressure within the barrel may be quickly decreased to zero by unlocking the slide lock and allowing the plunger to retreat.

A further embodiment of the invention incorporates a wireless transmission of pressure information from the pressure transducer to the readout display at the proximal end of the syringe. The transducer analog output may be introduced to a wireless transmitter to transmit an analog signal to the distal end of the syringe where a wireless receiver receives the signal, converts it to a digital signal, which is then introduced directly into the digital readout display.

The wireless transmitter may be an infrared (IR) processor/transmitter which receives the analog electrical signal, converts it into an infrared analog signal which is emitted from an IR emitter. The IR analog signal is transmitted through the body of the syringe preferably through an open channel to an IR analog receiver/converter at the proximal end of the syringe. Alternatively, the electrical signal may be converted into a digital IR or other digital wireless signal to be received by an appropriate receiver. An optical fiber may be advantageously used for precise IR transmission from the IR transmitter to the IR receiver. Further, a digital signal may be sent via an electrical conductor between the transducer/transmitter and the receiver/display.

The disclosure of U.S. Pat. Nos. 5,215,523 and 5,387,194 to Williams/Call et al. are incorporated herein by reference, especially with respect to means and systems for wireless transmission of signals produced by a pressure transducer. Also incorporated herein in its entirety by this reference is U.S. Pat. No. 5,021,046 to Wallace, especially the disclosure relating to pressure transducers.

Also, wireless transmission of pressure transducer information by radio signals may be utilized within the syringe for the purposes of the invention. However, radio signals may interfere with various other equipment in an operating room-type of environment and would generally be contraindicated where such a syringe was to be utilized upon a patient having a pacemaker.

Figure 8A:
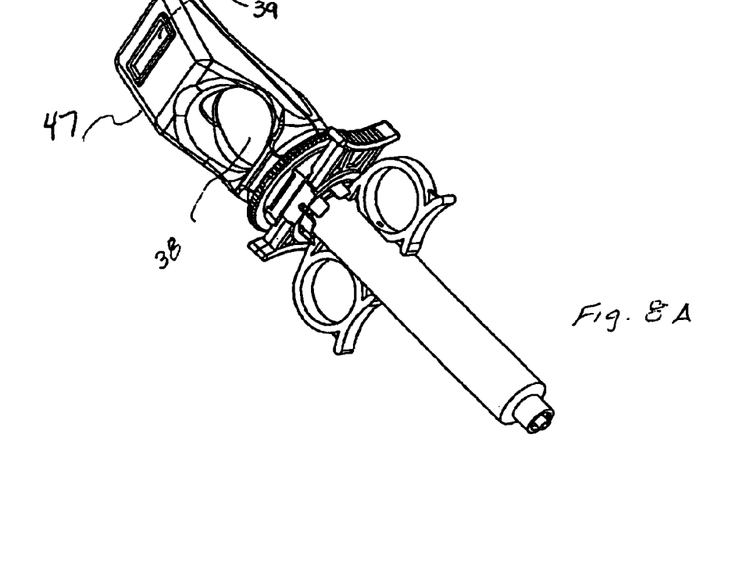
FIGS. 8A-8C are perspective views of a syringe with a streamlined block-shaped head containing the pressure display.
Figure 8B:
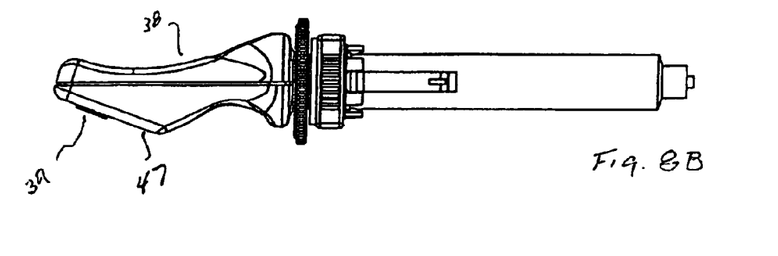
Figure 8C:
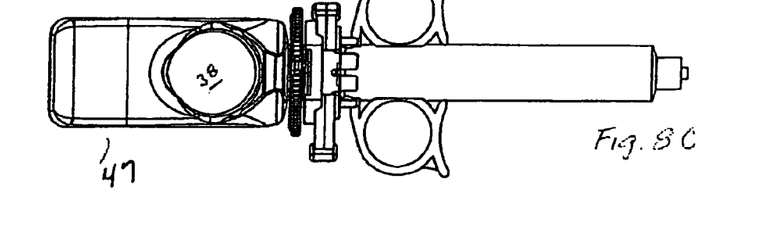

FIGS. 8A-8C are perspective views of a syringe with a pressure display head located in a display holder having a thumb aperture located between the display and the plunger.

FIG. 8A is a perspective view of a syringe with a pressure display head located in a display holder having a thumb aperture located between the display and the plunger. This particular syringe may incorporate the wired connection between the pressure transducer and the pressure display or a wireless transmission system such as that illustrated in FIG. 9.

FIGS. 8B and 8C show an elevational view and plan view, respectively, of the syringe (infuser) of FIG. 8A. The display holding portion 47 of the syringe is unique in appearance, as can be seen in FIGS. 8A, 8B and 8C. Additionally, the style, shape and juxtaposition of the various elements of the syringe further provide a syringe of a distinctive appearance.

FIG. 8C shows the bottom of the display holding portion 47, assuming that the surface in which the display is embedded is denoted the top surface, which is visible in FIGS. 8A and 8B.

The syringe of FIGS. 8A, 8B and 8C has the operator's thumb preferably inserted in a thumb aperture 38 from the bottom so that the display 39 will face upwards to the technician operating the syringe.

This particular syringe may incorporate the wired connection between the pressure transducer and the pressure display or a wireless transmission system such as that illustrated in FIG. 9, described hereinbelow.

Figure 9:
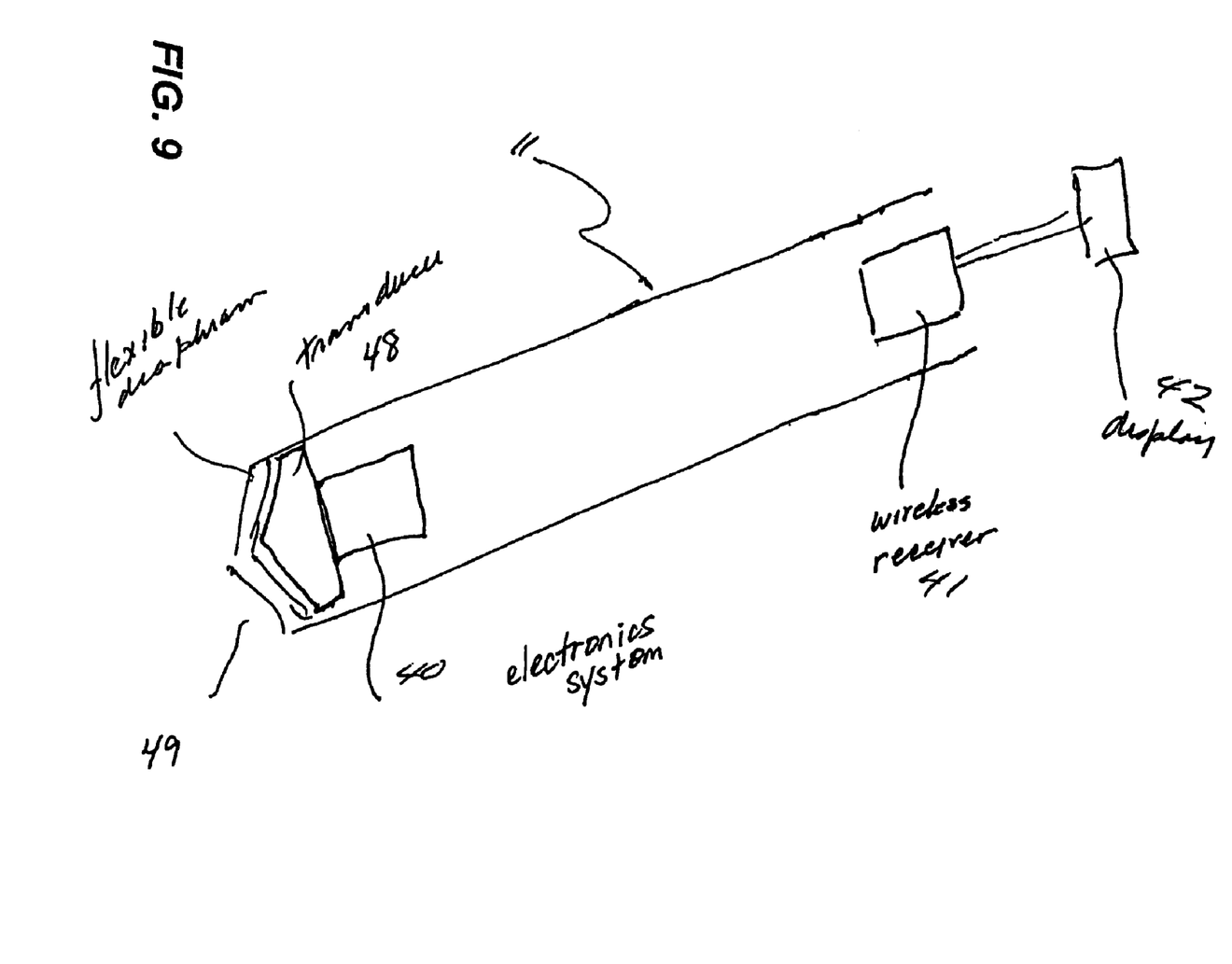
FIG. 9 is a cross-sectional view of a plunger having electronic means which transmits a wireless signal to a pressure display located at the proximal end of the plunger.

An embodiment of the invention is shown in FIG. 9 illustrating, in perspective view, a hollow plunger 11 having a pressure sensing transducer 48 located at or near the plunger tip 49 (distal end), which transducer 48 is electrically connected to an electronics system 40 which wirelessly transmits its output signal (IR or RF) to a remote receiver/pressure display 41 system. A display 42 may be located at or near the proximal end of the plunger 11 or at a remote location separate from the plunger 11, e.g., attached to an external surface of the syringe or entirely separate and remote from the syringe, e.g., on a support which positions the pressure display visible 42 to one or more members of a team involved in an infusion procedure.

The signal transmitted from the electronics system 40 to the display 42 may be an analog or a digital signal. If the signal is an analog signal, then the pressure display 42 includes a receiver mechanism which receives the signal and converts the analog signal to a digital signal suitable for being displayed as a pressure in millimeters of mercury, pounds per square inch, or other useful pressure units. The display 42 may further have a memory device whereby the total infusion procedure is recorded in terms of elapsed time and regular (substantially continuously, if desired) pressure recordings so that a history of the entire infusion procedure may be later downloaded for permanent storage.

A substantially hollow plunger having an internal pressure sensing mechanism, e.g., pressure transducer, in the tip, which is in direct or indirect contact with fluid of a syringe being pressurized, has many advantages, many of which have been enumerated herein. One such advantage is that a direct pressure reading may be displayed in a display incorporated in the proximal end of the plunger. Also, in a structure such as described herein, a fluid, preferably liquid, may be contained within the hollow plunger to contact a dynamic (diaphragm) type-pressure influenced mechanism and conduct the received pressure through the fluid, preferably liquid, to a pressure transducer/display in the proximal end of the plunger.

In such a structure, the pressure experienced at the tip of the plunger is transmitted by a fluid conductor to a pressure transducer or other pressure metering means, e.g., an analog pressure meter, at the proximal end of the plunger. Such a structure permits all the electronics necessary for a digital display, e.g., pressure transducer, analog/digital converter and digital signal receiving display to be directly coupled to one another and located at or near the proximal end of the hollow plunger.

Figure 10:
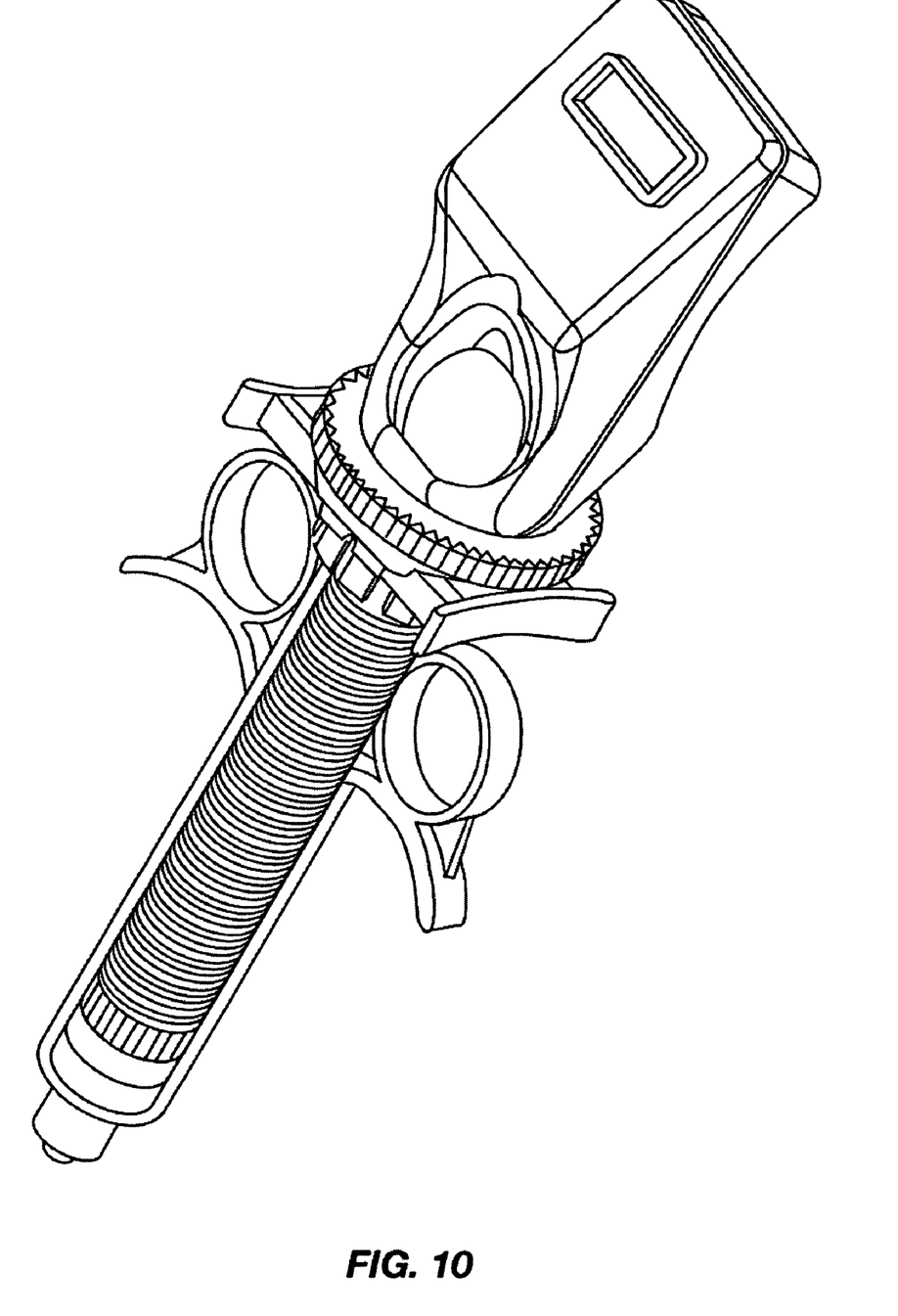
FIG. 10 is a perspective view of the syringe of FIGS. 8A-8C with fanciful display holder.

The display at the proximal end of the syringe may be incorporated into a housing of the varying shapes and designs shown herein which accommodate functional purposes. The shape of the display housing shown in FIGS. 8A-8C is particularly fanciful to provide a smooth aesthetic appearance while not diminishing its attributes as a display holder and thumb engagement device. A further perspective view of the syringe of FIGS. 8A-8C is shown in FIG. 10. The view is at an oblique angle from the rear of the syringe.

The above description is to aid in understanding the invention; the full scope of which is set forth herein in the appended claims.

What is claimed is:

1. A pressure applying and monitoring syringe, comprising:
    a barrel;
    a plunger configured to slide within the barrel and to apply pressure to a fluid within the barrel, said plunger comprising a pressure transducer at a distal end portion of said plunger that is configured to generate a signal proportional to the fluid pressure;
    a handle coupled to a proximal end portion of said plunger, said handle comprising an infrared receiver coupled to a display, wherein the pressure transducer is communicatively coupled to said infrared receiver, and wherein all of said handle is prevented from entering into said barrel;
    a first plunger advancement mechanism that is configured to provide to said plunger a sliding motion that is induced by thumb force at said handle;
    a second plunger advancement mechanism that is configured to provide to said plunger a sliding motion that is induced by a threaded mechanism to advance the plunger without requiring rotation of the plunger; and
    a switch for engaging either said first plunger advancement mechanism or said second plunger advancement mechanism.

2. The syringe of claim 1, in which pressure sensing electronics associated with said pressure transducer are incorporated into the plunger.

3. The syringe of claim 1, wherein the plunger is hollow and includes a fluid between a pressure influenced diaphragm at the distal end of the plunger and the pressure transducer.

4. A syringe comprising:
    a barrel;
    a piston configured to slide within the barrel and to apply pressure to a fluid within the barrel, the piston comprising a pressure transducer at a distal end portion of the piston that is configured to generate an electronic signal proportional to the fluid pressure;
    a handle coupled to a proximal end portion of said piston, said handle comprising an infrared receiver, wherein the pressure transducer is communicatively coupled to said infrared receiver to transmit the electronic signal to said infrared receiver from an infrared transmitter that is electrically connected to said pressure transducer;
    a first piston advancement mechanism that is configured to provide to said piston a sliding motion that is induced by force at said handle;
    a second piston advancement mechanism that is configured to provide to said piston a sliding motion that is induced by a threaded mechanism to advance the piston without requiring rotation of the piston; and
    a switch for engaging either said first piston advancement mechanism or said second piston advancement mechanism.

5. The syringe of claim 4, wherein the pressure transducer is connected electrically to electronic signal processing means associated with the piston.

6. The syringe of claim 4, wherein the handle further includes a display that is always maintained in a visible position to enable reading of the display while the pressure is applied to the fluid.

7. The syringe of claim 4 further comprising:
    electronic components to convert the electrical signal from the pressure transducer to a value that is rendered on a display.

8. The syringe of claim 4, wherein said signal from the pressure transducer is transmitted wirelessly to a remote display.

9. A fluid pressure inducing syringe comprising:
    a barrel;
    a plunger comprising a pressure transducer at a distal end portion of the plunger, wherein the plunger is configured to slide within the barrel to apply pressure to a fluid within the barrel, wherein the pressure transducer is configured to generate a signal proportional to the fluid pressure;
    a handle coupled to a proximal end portion of the plunger, the handle comprising a signal receiver, wherein the pressure transducer is communicatively coupled to said signal receiver to transmit said signal to said signal receiver from a signal transmitter that is communicatively coupled to said pressure transducer, and wherein said signal from the pressure transducer is transmitted wirelessly from said signal transmitter to said signal receiver;
    a first plunger advancement mechanism that is configured to provide a sliding motion of the plunger that is induced by force at the handle;
    a second plunger advancement mechanism that is configured to provide a sliding motion of the plunger that is induced by a threaded mechanism to advance the plunger without requiring rotation of the plunger, wherein the threaded mechanism includes a sleeve having a threaded portion encompassing at least a portion of the plunger, the sleeve freely rotatable about the plunger; and a switch for engaging either the first plunger advancement mechanism or the second plunger advancement mechanism.

10. The syringe of claim 9, wherein said sleeve and the switch have cooperative means configured to selectively permit rotational movement of the sleeve with respect to the locking mechanism when the second plunger advancement mechanism is engaged to cause minute axial motion of the sleeve and the plunger.

11. A fluid pressure inducing syringe comprising:

a barrel;

a plunger comprising a pressure transducer at a distal end portion of the plunger, wherein the plunger is configured to slide within the barrel to apply pressure to a fluid within the barrel, wherein the pressure transducer is configured to generate a signal proportional to the fluid pressure;

a handle coupled to a proximal end portion of the plunger, the handle comprising a signal receiver, wherein the pressure transducer is communicatively coupled to said signal receiver to transmit said signal to said signal receiver from a signal transmitter that is communicatively coupled to said pressure transducer and wherein said signal from the pressure transducer is transmitted wirelessly from said signal transmitter to said signal receiver, wherein said signal receiver is an infrared receiver and said signal transmitter is an infrared transmitter;

a first plunger advancement mechanism that is configured to provide a sliding motion of the plunger that is induced by force at the handle;

a second plunger advancement mechanism that is configured to provide a sliding motion of the plunger that is induced by a threaded mechanism to advance the plunger without requiring rotation of the plunger, wherein the threaded mechanism includes a sleeve having a threaded portion encompassing at least a portion of the plunger, the sleeve freely rotatable about the plunger; and a switch for engaging either the first plunger advancement mechanism or the second plunger advancement mechanism.

12. A fluid pressure inducing syringe comprising:

a barrel;

a plunger configured to slide within the barrel, said plunger comprising a pressure influenced diaphragm and a pressure transducer at a distal end portion of the plunger, the barrel and plunger together configured to generate a pressure on a fluid within the barrel, and wherein the pressure transducer is configured to generate a signal proportional to the fluid pressure;

a handle coupled to a proximal end portion of the plunger, the handle comprising a signal receiver communicatively coupled to a display that is configured for communicating the amount of fluid pressure generated, wherein the pressure transducer is communicatively coupled to the display through a signal transmitter and said signal receiver, and wherein all of the handle is prevented from entering into the barrel;

a first plunger advancement mechanism that is configured to provide to said plunger a sliding motion that is induced by force at said handle;

a second plunger advancement mechanism that is configured to provide to said plunger a sliding motion that is induced by a threaded mechanism to advance the plunger without requiring rotation of the plunger; and a switch for engaging either said first plunger advancement mechanism or said second plunger advancement mechanism.

13. The syringe of claim 12, wherein pressure information from the pressure transducer is wirelessly transmitted to the handle.

14. The syringe of claim 12, wherein pressure information from the pressure transducer is transmitted to the handle via an infra-red transmitter.

* * * * *